US005969825A

United States Patent [19]
Bomse et al.

[11] Patent Number: 5,969,825
[45] Date of Patent: Oct. 19, 1999

[54] DUAL-MODULATION LASER LINE-LOCKING FOR WAVELENGTH MODULATION SPECTROSCOPY

[75] Inventors: David S. Bomse; Joel A. Silver, both of Santa Fe, N.Mex.

[73] Assignee: Southwest Sciences Incorporated, N.Mex.

[21] Appl. No.: 08/846,591

[22] Filed: Apr. 30, 1997

Related U.S. Application Data

[63] Continuation-in-part of application No. 08/347,814, Nov. 30, 1994, which is a continuation of application No. 07/911,947, Jul. 10, 1992, abandoned, which is a continuation-in-part of application No. 07/740,798, Aug. 6, 1991, abandoned.

[51] Int. Cl.$^6$ ................................................. G01N 21/00
[52] U.S. Cl. ................................................. 356/437
[58] Field of Search .................... 356/437, 409, 356/326, 324, 325, 300; 250/343, 344; 324/96, 500, 501, 752

[56] References Cited

U.S. PATENT DOCUMENTS

| | | |
|---|---|---|
| 3,395,365 | 7/1968 | Fork . |
| 3,471,803 | 10/1969 | Forster . |
| 3,593,189 | 7/1971 | Buhrer . |
| 3,609,583 | 9/1971 | Brun . |
| 3,742,382 | 6/1973 | Smith . |
| 3,967,211 | 6/1976 | Itzkan et al. . |
| 4,297,035 | 10/1981 | Bjorklund . |
| 4,410,273 | 10/1983 | Mantz et al. . |
| 4,434,490 | 2/1984 | Kavaya et al. . |
| 4,594,511 | 6/1986 | Cooper et al. . |
| 4,765,736 | 8/1988 | Gallagher et al. . |
| 4,817,100 | 3/1989 | Cameron et al. . |
| 4,856,009 | 8/1989 | Hall et al. . |
| 4,932,775 | 6/1990 | Wissman et al. . |
| 4,937,448 | 6/1990 | Mantz et al. . |
| 5,047,639 | 9/1991 | Wong . |
| 5,267,019 | 11/1993 | Whittaker et al. . |
| 5,473,244 | 12/1995 | Libove et al. . |
| 5,652,526 | 7/1997 | Sullivan et al. . |
| 5,742,377 | 4/1998 | Minne et al. . |

FOREIGN PATENT DOCUMENTS

| | | |
|---|---|---|
| 3734401 | 4/1989 | Germany . |

OTHER PUBLICATIONS

"Double frequency modulation spectroscopy: high modulation frequency with low–bandwidth detectors," D.E. Copper, et al., *Applied Optics*, vol. 24, No. 9, pp. 1327–1332 (May 1, 1985).

"Modulation Broadening of NMR and ESR Line Shapes," G.V.H. Wilson, *J. Applied Physics*, vol. 34, pp. 3276–3285 (1963).

"Analytical Line Shapes for Lorentzian Signals Broadened by Modulation," R. Arndt, *J. Applied Physics*, vol. 36, pp. 2522–2524 (1965).

"Frequency Stabilization of Gas Lasers," A. White, *IEEE J. of Quantum Electronics*, vol. QE–1, No. 8, pp. 349–357 (1965).

"400 Hz frequency stability of a GaAlAs Laser frequency locked to the Rb(D2) line," T. Shay et al., *Optical Engineering*, vol. 29, No. 6, pp. 681–683 (1990).

"Harmonic Detection with Tunable Diode Lasers," D. Cassidy, et al., *Applied Physics*, vol. 29, pp. 279–285 (1982).

Bomse, D.S., "Dual–Modulation laser Line–Locking Scheme," *Applied Optics*, vol. 30, p. 2922, (Jul. 20, 1991).

(List continued on next page.)

*Primary Examiner*—K. P. Hantis
*Attorney, Agent, or Firm*—Jeffrey D. Myers; Brian J. Pangrle

[57] ABSTRACT

An improvement to a dual-modulation line-locking device for wavelength modulation spectroscopy employing a low-pass filter to generate a nonnormalized error signal and a bandpass filter and RMS-to-DC converter to generate a centering signal. When the error signal is approximately zero and the centering signal is large, the wavelength is coincident with the center of the absorption feature of the sample.

24 Claims, 3 Drawing Sheets

OTHER PUBLICATIONS

Sun and Whittaker, "Combined Wavelength and Frequency Modulation Spectroscopy: A Novel Diagnostic Tool for Materials Processing," *Applied Optics*, vol. 32, No. 6, pp. 885–893 (1993).

Sun and Whittaker, "Novel Etalon Fringe Rejection Technique for Laser Absorption Spectroscopy," *Applied Optics*, vol. 31, No. 24, pp. 4998–5002, (1992).

Sun and Whittaker, "Dynamic Resonant Peak Locking Scheme for Diode Laser Modulation Spectroscopy," *Optical Engineering*, vol. 32, No. 3, pp. 453–457 (1993).

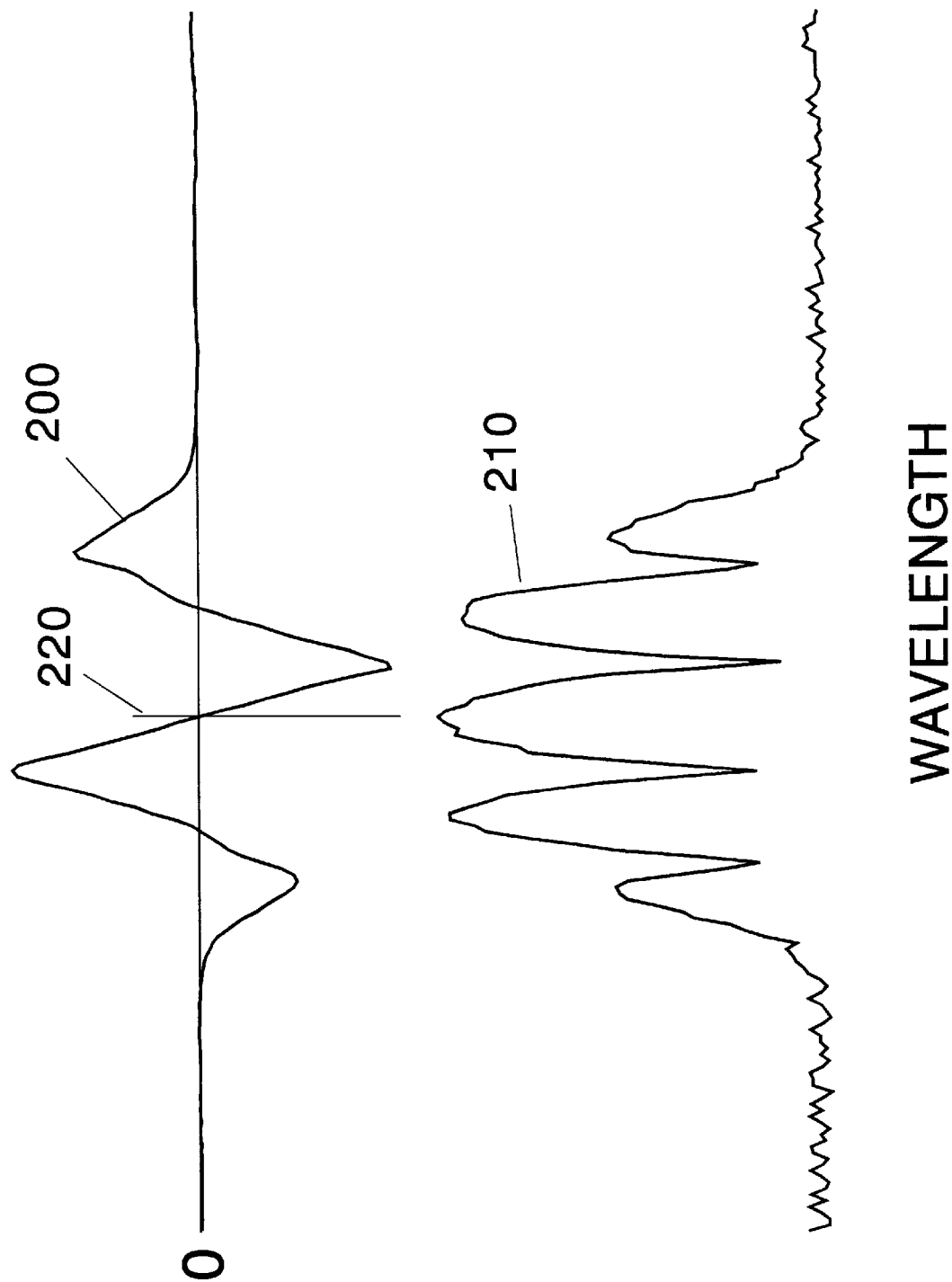

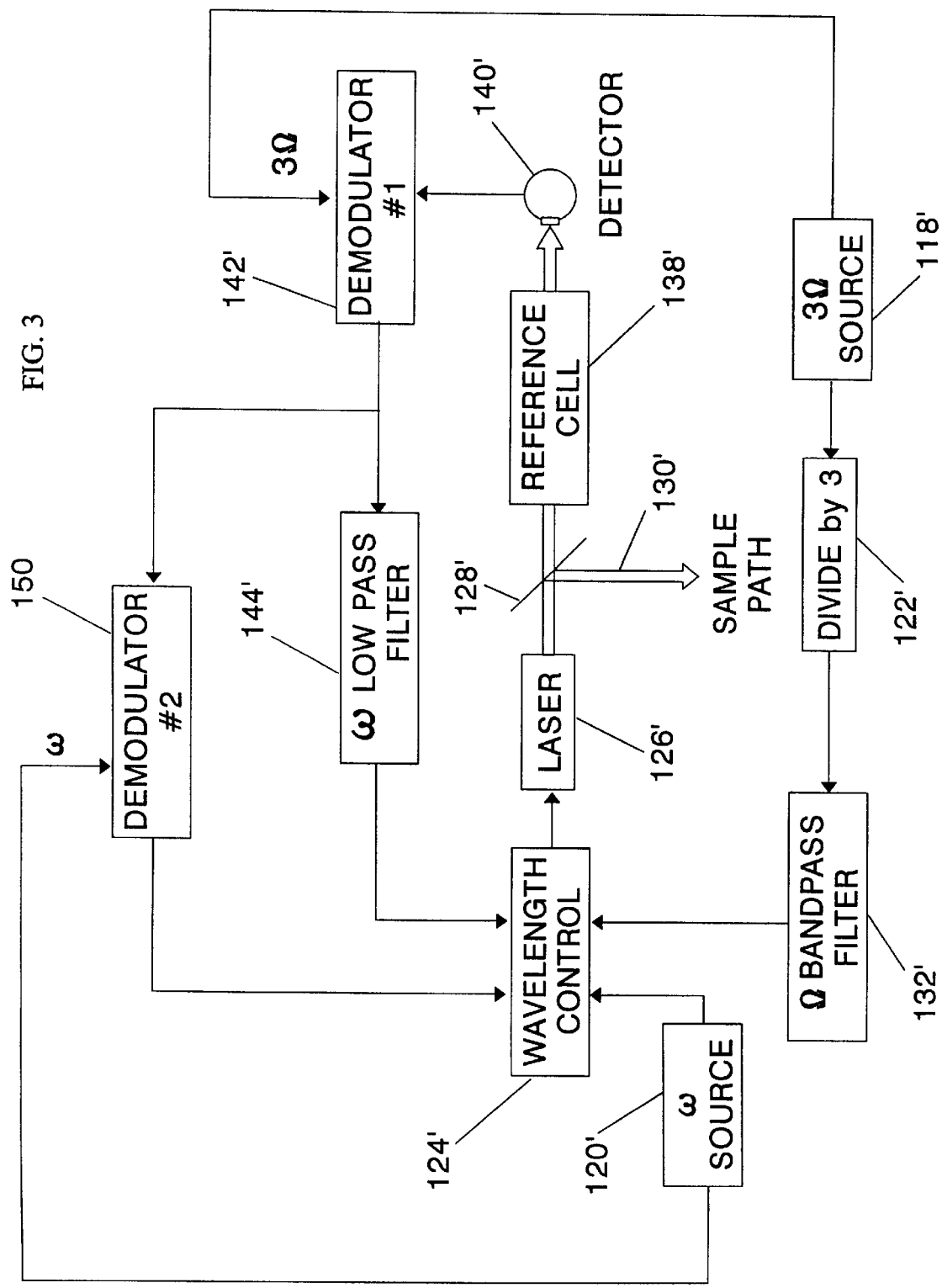

5,969,825

DUAL-MODULATION LASER LINE-LOCKING FOR WAVELENGTH MODULATION SPECTROSCOPY

CROSS-REFERENCE TO RELATED APPLICATIONS

This application is a continuation-in-part application of U.S. patent application Ser. No. 08/347,814, entitled "Dual Modulation Laser Line-Locking Technique for Wavelength Modulation Spectroscopy", to Bomse et al., filed on Nov. 30, 1994, which is a continuation application of U.S. patent application Ser. No. 07/911,947, entitled "Dual Modulation Laser Line-Locking Technique for Wavelength Modulation Spectroscopy", to Bomse, et al., filed on Jul. 10, 1992, now abandoned, which is a continuation-in-part application of U.S. patent application Ser. No. 07/740,798, entitled "Dual Modulation Laser Line-Locking for Wavelength Modulation Spectroscopy", to Bomse, filed on Aug. 6, 1991, now abandoned, the teachings of all of which are incorporated herein by reference.

BACKGROUND OF THE INVENTION

1. Field of the Invention (Technical Field)

The present invention relates to wavelength modulation spectroscopy.

2. Background Art

Dual-modulation line-locking, described in D. Bomse, *Applied Optics* 30:2922–4 (1991) and in the parent applications to the present application, listed above, is a useful application of optical spectroscopy for continuous monitoring of a selected species. The technique yields high sensitivity measurements of an optical absorbance generated by the target species while also providing simultaneous wavelength stabilization of a spectroscopic light source. In particular, dual-modulation line-locking improves wavelength modulation spectroscopy, which is a spectroscopic method that is easily implemented with wavelength tunable light sources such as diode lasers, by removing baseline fluctuations that add error to the absorbance measurements.

In Bomse's original dual-modulation line-locking method, the wavelength of a light source is modulated at two frequencies. Typically, a beam splitter diverts part of the light through a sample region and onto a detector such as a photodiode; the remainder of the light passes through a reference cell filled with an amount of the target species and then impinges on another detector. Optical absorption by the species in the sample and reference paths converts some of the wavelength modulation into synchronous amplitude modulations of the light, with the magnitude of the induced amplitude modulations being proportional to the size of the absorbances. The magnitude of the absorbance can be directly related to the absolute concentration of the absorbing species. Output from the sample leg detector is processed by two sequential demodulations to provide a signal that is proportional to the sample leg optical absorbance, hence proportional to the amount of target species within the path. One advantage of the sequential demodulation is that the absorbance measurement is free of baseline fluctuations. Output from the reference leg detector is also processed by two sequential demodulations, but the frequencies of the reference waveforms used for the demodulations are selected such that the demodulated spectral waveform can be used as a feedback signal for wavelength stabilization of the light source. Ideally, the reference leg signal is zero when the light source wavelength is coincident with the center wavelength of the absorption feature, and the signal varies linearly with small displacements from the center wavelength. This use of an optical absorbance for wavelength stabilization is generally known as line-locking and can be implemented using wavelength modulation spectroscopy as well as frequency modulation spectroscopy.

Two problems may arise, however, when implementing line-locking. The first occurs because the line-locking feedback signal can be approximately zero when the spectroscopic source wavelength is coincident with the center of the reference absorption feature or when the source wavelength is far removed from line center. The conventional line-locking signal cannot be used to distinguish between these two cases. The other problem arises when the amount of absorber material in the reference path changes. This introduces uncertainty into the amount of wavelength correction that needs to be applied in response to a given feedback signal. In other words, changing the amount of reference absorber material varies the gain of the feedback loop and can cause instabilities in the line-locking.

FIG. 3 is a schematic diagram of an undisclosed method (developed by the present inventors) that uses a second demodulator to provide a signal proportional to the optical absorbance within the reference leg optical path. The current applied to a diode laser 126' such as a Lasertron model QLM5S890-002 is modulated sinusoidally at two frequencies simultaneously, $\Omega=1$ MHz and $\omega=10$ kHz. It is well known that changing the current applied to a diode laser is a simple method for changing the wavelength of the laser light. The 1 MHz waveform is obtained by applying the output from a 3 MHz TTL oscillator 118' such as a Dale model X0-43B to a down counter 122' such as a Texas Instruments 74HC160N integrated circuit configured as a divide-by-three circuit component. Output from the counter is bandpass filtered 132' using a device similar to a TTE, Inc. series KC4-1M bandpass filter to produce a 1 MHz sine wave that is used as the first modulation frequency. The 10 kHz modulation waveform is supplied by a function generator 120' such as a Stanford Research Systems model DS345 function generator. The DC portion of the laser current is supplied by a current source such as an ILX model 3722b diode laser controller.

A beamsplitter 128' divides the laser beam into a sample leg portion 130' used for determining the absorbance of an unknown amount of the target species and a reference leg portion used for line-locking. The latter beam passes through a reference cell 138' filled with some of the target species and onto a photodiode detector 140' such as an Epitaxx ETX1000T InGaAs photodiode. The signal produced by the photodiode is demodulated using demodulator #1 142' such as a Mini-Circuits SRA-6 mixer; the local oscillator for the demodulator is supplied by the 3 MHz oscillator 118'.

Output from demodulator #1 is applied to a lowpass filter 144'. The lowpass filter is a device similar to a TTE, Inc. LC7-series filter and removes AC signal components at 1 MHz and 10 kHz (frequencies $\Omega$ and $\omega$) and their harmonics. Output from the lowpass filter provides the unnormalized error signal that is used for laser wavelength stabilization.

Output from demodulator #1 is also applied to demodulator #2 150 which uses frequency $\omega$ from source 120' as its local oscillator. Demodulator#2 150 is a device similar to Analog Devices AD630 integrated circuit. It produces a voltage proportional to the amplitude of the 10 kHz AC signal that is present on the output of demodulator #1 142'. When the laser wavelength is coincident with the center of the optical absorbance and the phase of the local oscillator is properly adjusted, the output of demodulator #2 150 is directly proportional to the optical absorbance in the reference path. Dividing the error signal obtained at the lowpass filter by the absorbance signal yields a normalized error signal that provides improved reliability for laser wavelength stabilization.

The present invention improves on dual-modulation line-locking by processing the line-locking signal to 1) verify that the light source wavelength is coincident with the absorption line center, and 2) maintain constant gain in the wavelength stabilization feedback loop.

SUMMARY OF THE INVENTION (DISCLOSURE OF THE INVENTION

The present invention is an improvement to a dual-modulation line-locking devices and methods for wavelength modulation spectroscopy comprising: a lowpass filter receiving a signal from the demodulator and providing a signal to the wavelength control element; a signal conditioning filter receiving a signal from the demodulator; and an RMS-to-DC converter receiving a signal from the bandpass filter and generating a signal to the wavelength control element. In the preferred embodiment, the lowpass filter removes AC signal components at two modulation frequencies and harmonics thereof, most preferably at approximately 1 MHz and 10 kHz and harmonics thereof, and provides an unnormalized error signal to the wavelength control element. The signal conditioning filter (preferably a bandpass or lowpass filter) provides a signal to the RMS-to-DC converter with components at approximately 10 kHz. The RMS-to-DC converter generates a voltage signal proportional to a root-mean-squared amplitude of the signal from the demodulator, preferably of components at approximately 10 kHz of the signal from the demodulator. The wavelength control element divides the signal provided by the lowpass filter by the signal generated by the RMS-to-DC converter to provide a normalized error signal. The signal generated by the RMS-to-DC converter preferably has an odd number of lobes when the laser wavelength is scanned slowly across the absorption feature. The wavelength control element then stabilizes the subject wavelength so as to maintain the signal from the lowpass filter at approximately zero and the signal from the RMS-to-DC converter at a positive value corresponding approximately to a line center absorbance.

A primary object of the present invention is to improve normalization of the error signal within dual-modulation line-locking devices for wavelength modulation spectroscopy.

Another object of the invention is to improve reliability of the wavelength stabilization component within dual-modulation line-locking devices for wavelength modulation spectroscopy by using the absorbance signal to confirm proper operation of the line-locking feedback loop.

A primary advantage of the present invention is its efficacy in single detector systems.

Another advantage of the present invention is that an RMS-to-DC converter can replace the second demodulator, the RMS-to-DC converter not requiring a local oscillator or demodulation phase control.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 2 contrasts graphs as a function of laser wavelength of the unnormalized error signal from a lowpass filter used within the invention and the RMS-to-DC waveform signal; and FIG. 3 is a schematic diagram of a method on which the invention improves.

Figure 1:
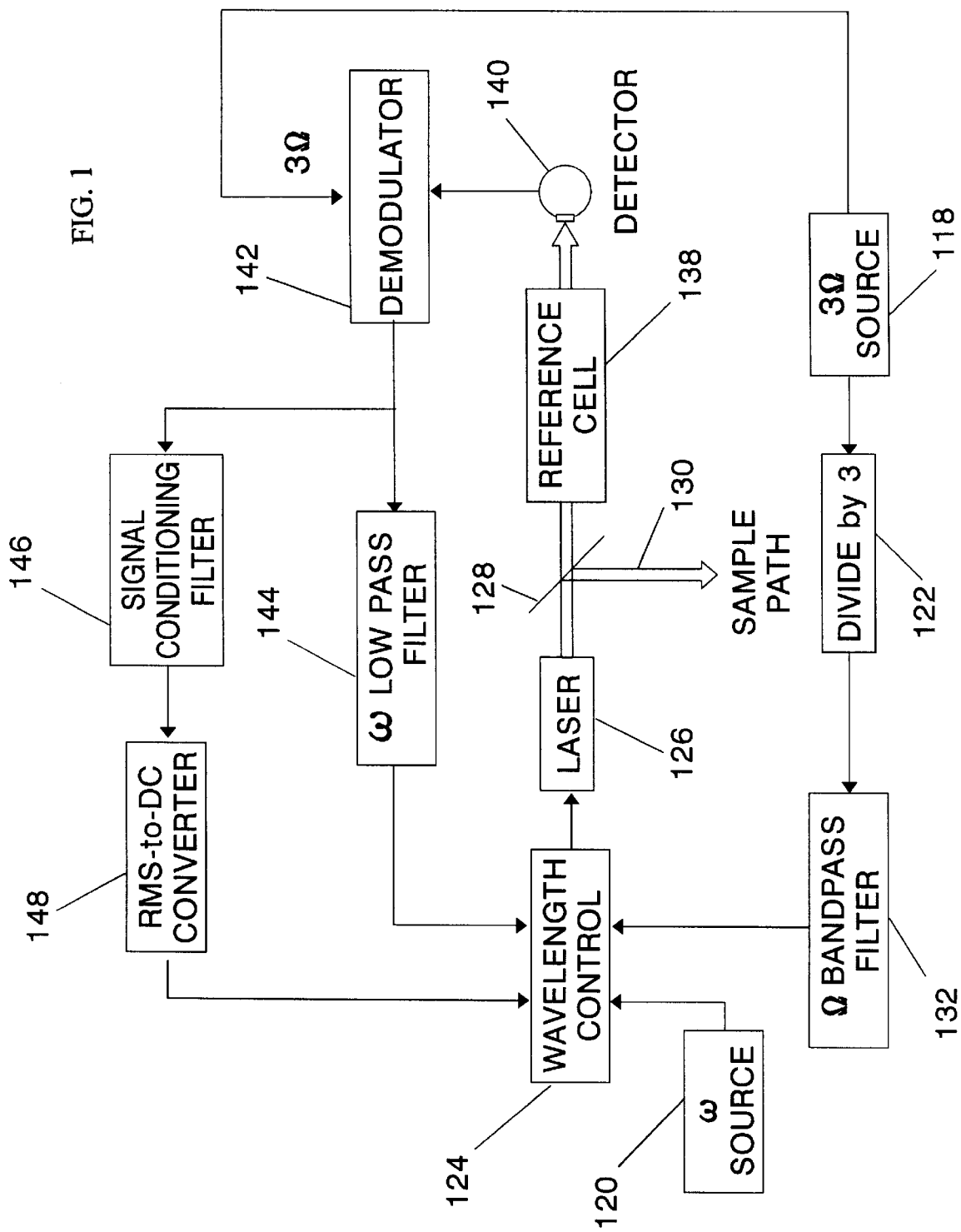
FIG. 1 is a schematic diagram of the preferred embodiment of the invention.

DESCRIPTION OF THE PREFERRED EMBODIMENTS (BEST MODES FOR CARRYING OUT THE INVENTION)

The present invention improves the method and apparatus used to process the signal from the reference path detector when dual-modulation line-locking is used. The spectroscopic light source (typically a continuously tunable laser such as a diode laser) is wavelength modulated at two frequencies simultaneously. These frequencies are $\Omega$ and $\omega$, with $\Omega \gg \omega$. The reference optical path uses a portion of the light beam that is directed through a region containing the target species and onto a photodetector such as a photodiode. Enough of the target species is present along this reference optical path to provide an optical absorbance that is useful for wavelength stabilization.

The output signal from the reference path photodetector is demodulated at an odd harmonic of the larger modulation frequency, $\Omega$. Odd harmonics can include the fundamental frequency. A portion of the demodulated signal is applied to a lowpass electronic filter which removes frequencies $\Omega$ and $\omega$ and their higher harmonics from the output of the demodulator. Output from the lowpass filter is useful for wavelength stabilization because the output varies linearly with wavelength for small changes in wavelength about the center of the optical absorption feature.

A second portion of the output from the demodulator is used to generate a signal proportional to the reference cell absorbance. In one method, the signal from the demodulator is applied to an RMS-to-DC converter. This electronic component generates a signal proportional to the AC component at frequency $\omega$. A large signal is produced by the RMS-to-DC converter when the light source wavelength is coincident with the center of the optical absorption feature. A second method for generating a signal proportional to the reference path absorbance uses a second demodulator synchronized to frequency $\omega$. In both methods, the resulting signal is proportional to the optical absorbance in the reference path and is used for two purposes. First, the absorbance signal is an indicator of line-locking performance; the line-locking apparatus is performing well when the error signal is small and the absorbance signal is large. If, on the other hand, the wavelength is far removed from line center, then both the error signal and the absorbance signal will be near zero (after any necessary baseline subtraction).

Secondly, the absorbance signal corrects the gain of the line-locking feedback loop. Since both the slope of the line-locking error signal and the magnitude of the absorbance signal are proportional to the optical absorbance in the reference path, then dividing the error signal by the absorbance signal provides a line-locking discriminant that maintains nearly fixed feedback gain despite changes in the reference path optical absorbance. The resulting normalized feedback signal is more useful for line-locking than is the uncorrected error signal.

The choice of signal processing method—whether to use the RMS-to-DC converter circuitry or a second demodulator—represents a tradeoff between the ease of implementation of the RMS-to-DC converter, which does not require a local oscillator or phase adjustment, and the better signal-to-noise ratio available from the demodulator. This increased noise is usually not the limiting factor in achieving line-locking stability.

FIG. 1 is a schematic diagram of the preferred embodiment of the invention. The current applied to a diode laser 126 such as a Lasertron model QLM5S890-002 is modulated sinusoidally at two frequencies simultaneously, $\Omega=1$ MHz and $\omega=10$ kHz. It is well known that changing the current applied to a diode laser is a simple method for changing the wavelength of the laser light. The 1 MHz waveform is obtained by applying the output from a 3 MHz TTL oscillator 118 such as a Dale model X0-43B to a down counter 122 such as a Texas Instruments 74HC160N integrated circuit configured as a divide-by-three circuit component. Output from the counter is bandpass filtered 132 using a device similar to a TTE, Inc. series KC4-1M bandpass filter to produce a 1 MHz sine wave that is used as the first modulation frequency. The 10 kHz modulation waveform is supplied by a function generator 120 such as a Stanford Research Systems model DS345 function generator. The DC portion of the laser current is supplied by a current source such as an ILX model 3722b diode laser controller.

A beamsplitter 128 divides the laser beam into a sample leg portion 130 used for determining the absorbance of an unknown amount of the target species and a reference leg portion used for line-locking. The latter beam passes through a reference cell 138 filled with some of the target species and onto a photodiode detector 140 such as an Epitaxx ETX1000T InGaAs photodiode. The signal produced by the photodiode is demodulated using a demodulator 142 such as a Mini-Circuits SRA-6 mixer; the local oscillator for the demodulator is supplied by the 3 MHz oscillator 118.

Output from the demodulator is applied to a lowpass filter 144 and to signal conditioning filter 146. The lowpass filter is a device similar to a TTE, Inc. LC7-series filter and removes AC signal components at 1 MHz and 10 kHz (frequencies $\Omega$ and $\omega$) and their harmonics. Output from the lowpass filter provides the unnormalized error signal that is used for laser wavelength stabilization.

The signal conditioning filter 146 is preferably a bandpass filter device similar to a TTE, Inc. KB3-10K-6K filter and transmits to the RMS-to-DC converter 148 only AC signal components at or near 10 kHz (frequency $\omega$). The RMS-to-DC converter 148 is a component similar to an Analog Devices model AD536A integrated circuit. It produces a voltage proportional to the root-mean-squared amplitude of the 10 kHz AC signal that is present on the output of demodulator 142. When the laser wavelength is coincident with the center of the optical absorbance, the RMS-to-DC signal is directly proportional to the optical absorbance in the reference path. Dividing the error signal obtained at the lowpass filter by the RMS-to-DC signal yields a normalized error signal that provides improved reliability for laser wavelength stabilization. Alternatively, the signal conditioning filter may be a lowpass filter that transmits frequency $\omega$ (10 kHz in the preferred embodiment) because $\omega$ is the lowest AC frequency used in the system and the RMS-to-DC coverter does not respond to frequencies near DC.

FIG. 2 shows key spectral waveforms generated by the signal processing components in the preferred embodiment. The nominal diode laser wavelength was set to be coincident with the hydrogen cyanide P(17) rotational line at 6463.66 $cm^{-1}$. For this experiment, the line-locking feedback loop was disabled. The DC portion of the laser current was stepped slowly across the absorption feature; the upper trace 200 shows the unnormalized error signal obtained from lowpass filter 144. Not surprisingly, the spectral waveform looks similar to a third-harmonic wavelength modulation spectrum shown in FIG. 1c of Bomse. The error signal is zero when the wavelength is coincident with the center of the absorption line (indicated by the vertical line 220) and varies linearly with small changes in laser wavelength around that point. The RMS-to-DC waveform 210 consists of a five lobes. The peak of the center lobe also coincides with the center of the absorption feature.

As expected, both the wavelength stabilization error signal 200 and the RMS-to-DC signal 210 go to zero at wavelengths far removed from the absorption feature. Thus, the first advantage of the present invention is demonstrated: the RMS-to-DC signal helps verify correct operation of the line-locking feedback loop. The laser wavelength is properly stabilized when the error signal is near zero and the RMS-to-DC signal is large.

Since the magnitude of the RMS-to-DC peak signals is proportional to the optical absorbance within the reference path, the center peak of the RMS-to-DC signal can be used to normalize the error signal, thereby providing constant gain within the feedback loop used for wavelength stabilization.

The present invention can be configured for use with a single optical path functioning as both sample and reference paths. Only one detector need be used. In this case, output from the detector is divided between circuitry used to determine the total optical absorbance (where the circuitry is similar to the signal processing methods described in the U.S. patent application Ser. No. 08/347,814 and in Bomse) and circuitry such as shown in FIG. 1 used for wavelength stabilization. It is assumed that there is always a sufficient amount of the target material within the optical path to provide a useable signal for wavelength stabilization. The present invention is particularly useful for such single path systems because it is likely that the total amount of target species may vary widely in time; normalization of the error signal is important to guarantee wavelength stability.

Another advantage of the present invention is that the RMS-to-DC signal processing step can also replace the second demodulation step in processing the output from the sample path detector. An RMS-to-DC converter does add some noise compared with a using a demodulator such as a mixer or lock-in amplifier, but is simpler to implement because the RMS-to-DC converter does not require a local oscillator or demodulation phase control.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application(s), are hereby incorporated by reference.

What is claimed is:

1. In a dual-modulation line-locking device for wavelength modulation spectroscopy comprising a demodulator and wavelength control means, an improvement comprising:

a lowpass filter receiving a signal from the demodulator and providing a signal to the wavelength control means;

a signal conditioning filter receiving a signal from the demodulator; and an RMS-to-DC converter receiving a signal from said signal conditioning filter and generating a signal to the wavelength control means.

2. The improvement of claim 1 wherein said lowpass filter removes AC signal components at two modulation frequencies and harmonics thereof.

3. The improvement of claim 2 wherein said lowpass filter removes AC signal components at approximately 1 MHz and 10 kHz and harmonics thereof.

4. The improvement of claim 1 wherein said lowpass filter provides an unnormalized error signal to the wavelength control means.

5. The improvement of claim 1 wherein said signal conditioning filter provides a signal to said RMS-to-DC converter comprising components at approximately 10 kHz.

6. The improvement of claim 1 wherein said signal conditioning filter is selected from the group consisting of bandpass filters and lowpass filters.

7. The improvement of claim 1 wherein said RMS-to-DC converter generates a voltage signal proportional to a root-mean-squared amplitude of the signal from the demodulator.

8. The improvement of claim 7 wherein said RMS-to-DC converter generates a voltage signal proportional to a root-mean-squared amplitude of components at approximately 10 kHz of the signal from the demodulator.

9. The improvement of claim 1 wherein the wavelength control means comprises means for dividing said signal provided by said lowpass filter by said signal generated by said RMS-to-DC converter to provide a normalized error signal.

10. The improvement of claim 1 wherein said signal generated by said RMS-to-DC converter consists substantially of an odd number of lobes.

11. The improvement of claim 10 wherein a peak of one of said lobes corresponds to a center of an absorption feature of a sample.

12. The improvement of claim 1 wherein the wavelength control means comprises means for stabilizing a wavelength to maintain the signal from said lowpass filter at approximately zero and the signal from said RMS-to-DC converter at a positive value corresponding approximately to a line center absorbance.

13. In a dual-modulation line-locking method for wavelength modulation spectroscopy employing a demodulated signal and wavelength control, an improved method comprising the steps of:

(a) lowpass filtering the demodulated signal to generate a first wavelength control signal;

(b) filtering the demodulated signal; and (c) RMS-to-DC converting the filtered signal and generating therefrom a second wavelength control signal.

14. The improved method of claim 13 wherein lowpass filtering comprises removing AC signal components at two modulation frequencies and harmonics thereof.

15. The improved method of claim 14 wherein lowpass filtering comprises removing AC signal components at approximately 1 MHz and 10 kHz and harmonics thereof.

16. The improved method of claim 13 wherein lowpass filtering comprises generating an unnormalized error signal as the first wavelength control signal.

17. The improved method of claim 13 wherein filtering comprises generating a signal for RMS-to-DC converting comprising components at approximately 10 kHz.

18. The improved method of claim 13 wherein filtering comprises filtering selected from the group consisting of bandpass filtering and lowpass filtering.

19. The improved method of claim 13 wherein RMS-to-DC converting comprises generating a voltage signal proportional to a root-mean-squared amplitude of the demodulated signal as the second wavelength control signal.

20. The improved method of claim 18 wherein RMS-to-DC converting comprises generating a voltage signal proportional to a root-mean-squared amplitude of components at approximately 10 kHz of the demodulated signal.

21. The improved method of claim 13 additionally comprising the step of dividing the first wavelength control signal by the second wavelength control signal to provide a normalized error signal.

22. The improved method of claim 13 wherein RMS-to-DC converting comprises generating a second wavelength control signal consisting substantially of an odd number of lobes.

23. The improved method of claim 22 wherein RMS-to-DC converting comprises generating a second wavelength control signal consisting substantially of an odd number of lobes, wherein a peak of one of the lobes corresponds to a center of an absorption feature of a sample.

24. The improved method of claim 13 additionally comprising the step of stabilizing a wavelength to maintain the first wavelength control signal at approximately zero and the second wavelength control signal at a positive value corresponding approximately to a line center absorbance.

* * * * *